(12) United States Patent
Maury et al.

(10) Patent No.: US 12,268,573 B2
(45) Date of Patent: Apr. 8, 2025

(54) TOOL FOR USE IN DENTAL IMPLANT TREATMENTS AND RETENTION ELEMENT

(71) Applicant: STRAUMANN HOLDING AG, Basel (CH)

(72) Inventors: Damien Maury, Basel (CH); Stéphane Courvoisier, Basel (CH); Azagen Mootien, Basel (CH); Florian Dalla Torre, Basel (CH)

(73) Assignee: STRAUMANN HOLDING AG, Basel (CH)

( * ) Notice: Subject to any disclaimer, the term of this patent is extended or adjusted under 35 U.S.C. 154(b) by 810 days.

(21) Appl. No.: 17/285,578

(22) PCT Filed: Oct. 14, 2019

(86) PCT No.: PCT/EP2019/077793
§ 371 (c)(1),
(2) Date: Apr. 15, 2021

(87) PCT Pub. No.: WO2020/078911
PCT Pub. Date: Apr. 23, 2020

(65) Prior Publication Data
US 2022/0000589 A1    Jan. 6, 2022

(30) Foreign Application Priority Data
Oct. 15, 2018   (EP) ..................... 18200552

(51) Int. Cl.
*A61C 8/00*    (2006.01)
*B25B 15/00*   (2006.01)
*B25B 23/00*   (2006.01)

(52) U.S. Cl.
CPC .......... *A61C 8/0089* (2013.01); *B25B 15/001* (2013.01); *B25B 23/0035* (2013.01)

(58) Field of Classification Search
CPC . A61C 8/0087; A61C 8/0089; A61B 17/8841; A61B 17/8872–8894;
(Continued)

(56) References Cited

U.S. PATENT DOCUMENTS 5,538,428 A   7/1996  Staubli
5,622,500 A   4/1997  Niznick
(Continued)

FOREIGN PATENT DOCUMENTS

CN   104905871 A    9/2015
DE   198 60 060 A1  7/2000
(Continued)

OTHER PUBLICATIONS

Jul. 1, 2022 Office Action issued in Chinese Patent Application No. 201980079888.3.
(Continued)

*Primary Examiner* — Edward Moran
(74) *Attorney, Agent, or Firm* — Oliff PLC

(57) ABSTRACT

A tool for use in dental implants. The tool includes a retention element held in the tool shaft via a friction fit. The retention element is adapted to grip a variety of impact drivers via a frictional fit for use in tightening procedures of a dental procedure. The tool also includes a variety of features for interaction with additional dental instruments, or that aid in cleaning and sanitization of the tool.

14 Claims, 16 Drawing Sheets

(58) Field of Classification Search
CPC ... A61B 17/92; A61B 17/921; B25B 23/0085; B25B 23/0035; B25B 23/0078; B25B 23/08; B25B 23/10; B25B 23/105
See application file for complete search history.

(56) References Cited

U.S. PATENT DOCUMENTS

| | | | | |
|---|---|---|---|---|
| 5,961,330 | A * | 10/1999 | Hanson | A61C 8/0087 433/77 |
| 5,979,643 | A * | 11/1999 | Blonder | A61B 50/33 206/459.5 |
| 6,524,035 | B1 | 2/2003 | Robison | |
| 7,121,829 | B2 * | 10/2006 | Day | A61C 8/0087 433/163 |
| 7,451,870 | B2 * | 11/2008 | Donahoe | A61B 50/30 220/826 |
| 9,492,249 | B1 | 11/2016 | Efman et al. | |
| 2001/0005576 | A1 | 6/2001 | Rogers et al. | |
| 2001/0019816 | A1 | 9/2001 | Kumar | |
| 2011/0143316 | A1 | 6/2011 | Olson et al. | |
| 2011/0196380 | A1 | 8/2011 | Cremer et al. | |
| 2015/0257797 | A1 * | 9/2015 | Biedermann | A61B 17/7082 606/305 |
| 2015/0374426 | A1 | 12/2015 | Galm et al. | |
| 2020/0000559 | A1 | 1/2020 | Chung | |

FOREIGN PATENT DOCUMENTS

| | | |
|---|---|---|
| EP | 1 013 237 A2 | 6/2000 |
| EP | 2 918 238 A1 | 9/2015 |
| EP | 3 332 735 A1 | 6/2018 |
| KR | 10-2018-0103693 A | 9/2018 |
| WO | 01/50978 A1 | 7/2001 |

OTHER PUBLICATIONS

Apr. 23, 2020 International Search Report issued in International Patent Application No. PCT/EP2019/077793.
Apr. 23, 2020 Written Opinion issued in International Patent Application No. PCT/EP2019/077793.

* cited by examiner

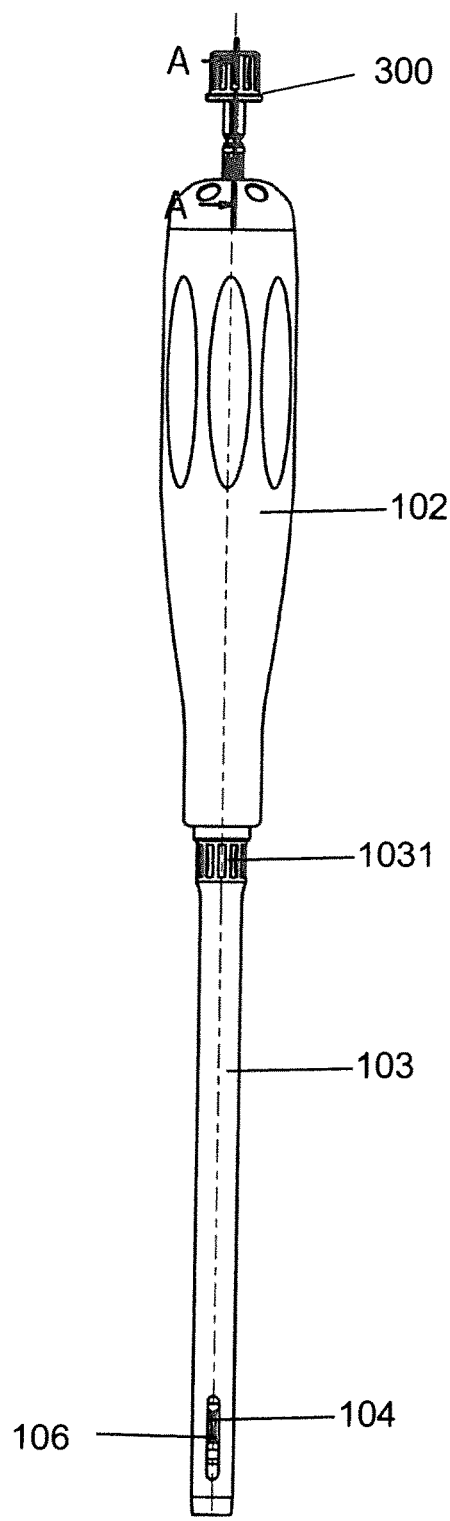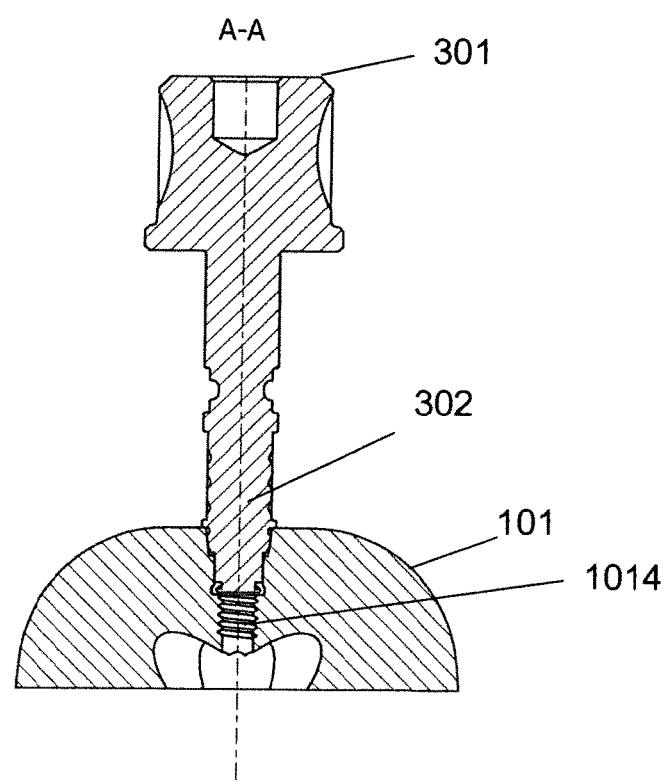
Fig. 12A
Fig. 12B

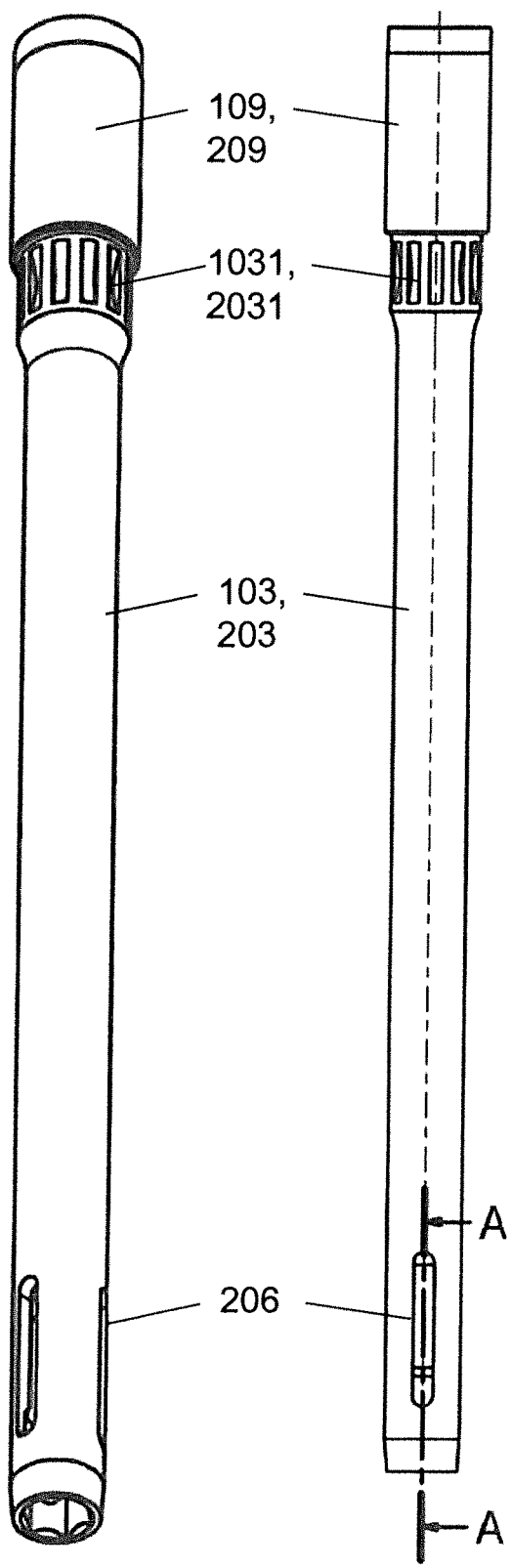
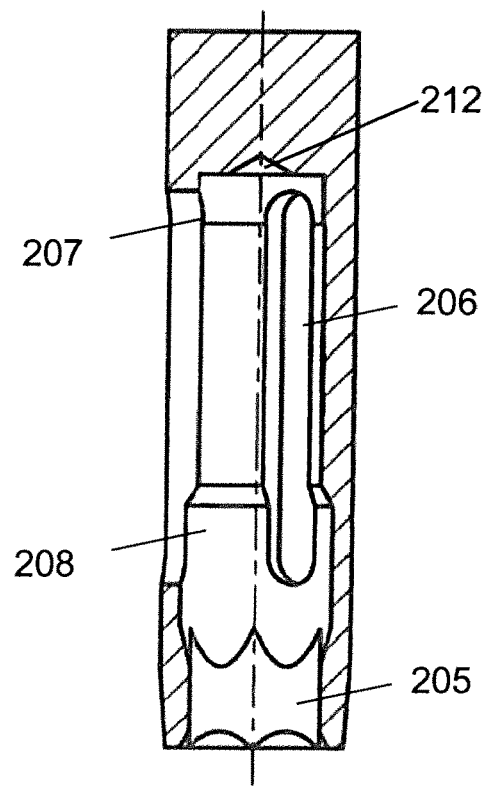
Fig. 15A      Fig. 15B      Fig. 15C

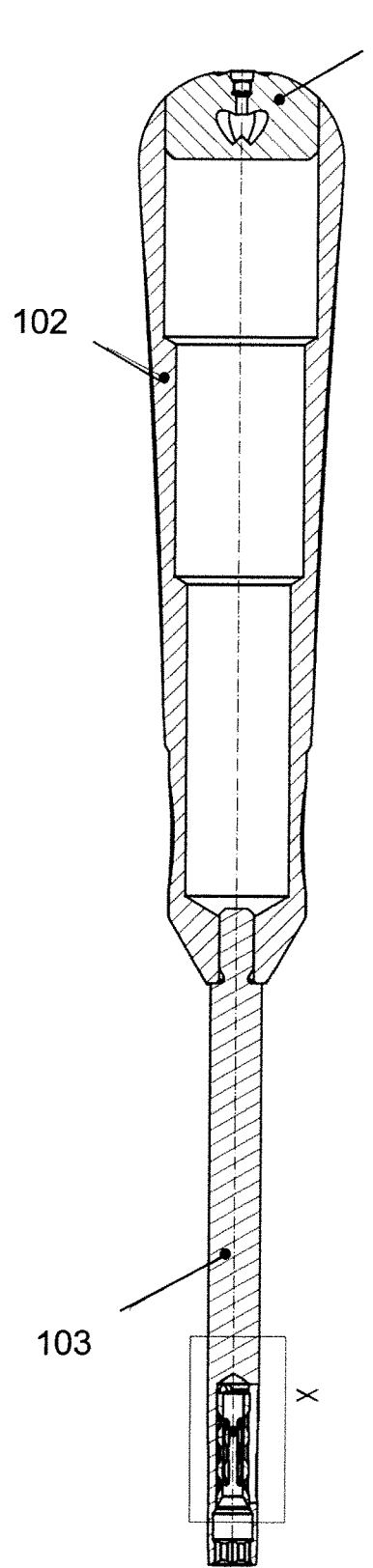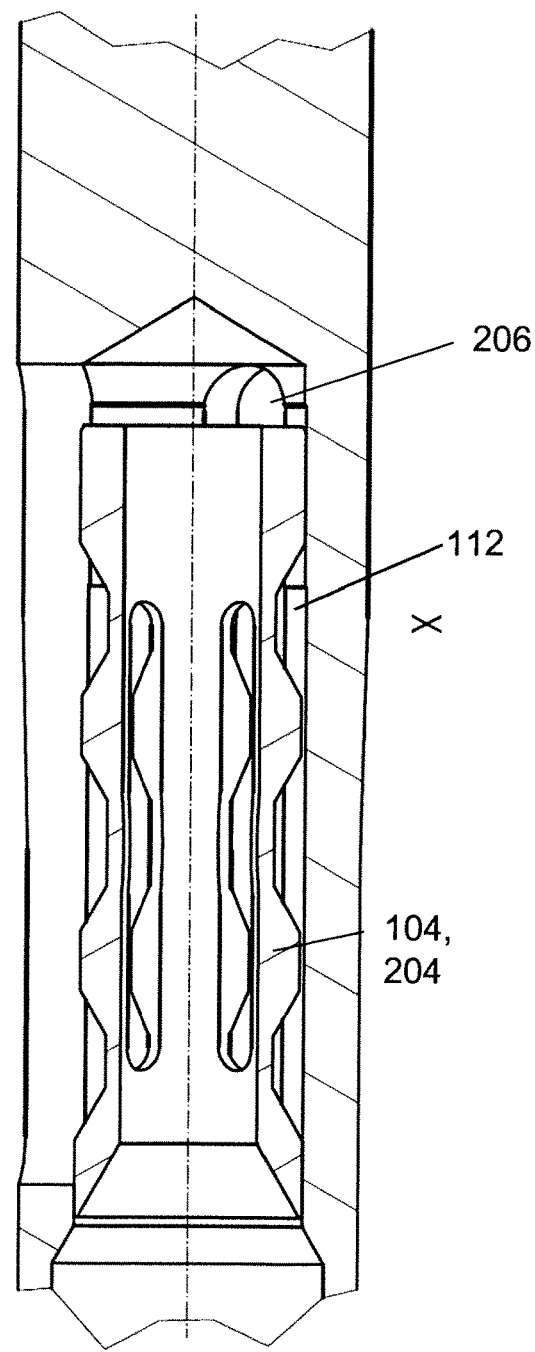
Fig. 16A
Fig. 16B

TOOL FOR USE IN DENTAL IMPLANT TREATMENTS AND RETENTION ELEMENT

BACKGROUND ART

In the field of dental practice, a wide variety of surgical procedures involve the implanting of a component to replace damaged or missing teeth, in particular dental roots. These components may take the form of a crown, bridge, or denture, and are secured in the jaws of the patient via a dental implant, which is screwed in the jaw bone.

Said implant is placed in the jaw and allowed to heal, commonly with a healing abutment attached to it in case of a one stage implant placement, before a dental prosthetic is added. During the tooth replacement an abutment is attached to the implant. This abutment may be screwed into the implant such that it is securely fastened and provides a protrusion from the gum, onto which a crown may be attached via screws or a dental cement.

The screwing of various components including the abutment or implant facilitates the need for a driver, a small screwdriver (also referred to as implant driver, if suitable for inserting an implant) which, via a complimentary shape can be used to convey torque to the abutment or implant, thus allowing for either tightening or loosening steps to be performed.

Implant drivers, which have various shapes and sizes depending upon their intended function and the respective implant system, are generally small enough that they can easily fit into the mouth of a patient. Implant drivers, however, may have a standardized shaft portion which allows the implant driver to be connected to a dental handpiece or may have a head adapted for use with a ratchet. However, the small size of these implant drivers often mean that they may only be gripped between finger and thumb, thus preventing a large amount of torque to be transferred.

As such, it is useful for a dental professional to have an adaptor capable of holding the implant driver securely, but allowing for a far larger area to be gripped by the hands of a medical professional.

However, due to the varying shapes of implant drivers, it is generally costly for a full size screwdriver (or adapter for such) to be procured for each individual implant driver. In addition, this leads to greater number of instruments required to be kept on hand for a dental procedure, thus further complicating the role of the dental professional.

It is thus an object of the present invention to provide a dental screwdriver and/or a component for a dental screwdriver, which can retain a variety of different shaped implant drivers, without the need for individual adapters.

Furthermore, screwdrivers which can hold implant drivers, much like the majority of dental equipment, require frequent cleaning and sterilization such that the equipment may be sanitized, during, or between procedures.

As such, it is a further object of the present invention to provide a dental screwdriver, which includes features that render the cleaning and sterilization of the screwdriver far easier and/or more efficient.

Whilst a dental screwdriver holding an implant driver is intended to generally be operated by hand, it may often be required that a ratcheting device is used to ensure that the correct degree of torque is provided and that the dental components are tightened to a certain standard.

It is thus a further object of the present invention to provide a dental screwdriver with features that would allow for interaction with a ratcheting device such that a specific level of torque can be applied by a dental professional.

Finally, it is noted that when using small components such as implant drivers, abutments and tooth crowns, these are not easily held such that they can be retrieved quickly and often need to be set aside in a specific holding tray such that they are not confused for other components or lost. Furthermore, it is often an extended process, should a crown or abutment need to be modified slightly, as the crown or abutment needs to be held securely, which may not be able to be performed quickly and easily during a dental procedure.

Thus it is a further aim of the present invention to provide for a feature which would allow for components such as dental screwdrivers and/or abutments to be held securely, thus allowing the dental professional to retrieve said feature quickly when it is needed. It is also thus an aim to provide a feature by which a crown and/or an abutment may be modified easily.

SUMMARY

One or more of the problems outlined above are solved by the tools according to claims 1 and 10 and/or by the retention element according to claim 6. The dependent claims describe preferred embodiments of the invention.

One aspect of the present invention relates to a tool used for securing dental components. Said tool comprising a handle by which it may be gripped by a user and rotated such that a rotational force may be provided to a dental component. The dental tool further comprising a shaft connected to the handle wherein the distal end of the shaft (the end not connected to the handle) comprises a mounting section which may facilitate interaction between the dental tool and the dental component to be tightened (or loosened) by holding a retention element within the mounting section of the shaft. Said retention element is securely held in the shaft and is adapted to securely hold an implant driver while torque delivered to the tool may be transferred to the implant driver and thus the dental component to be tightened. It should be noted herein that reference to the tightening of a dental component also encompasses the loosening of said component.

The dental tool may have the shape or is configured as a screwdriver or handle driver. The handle, the shaft, and the mounting section are preferably aligned along a common axis which defines the longitudinal direction of the dental tool. Thus, the handle and the shaft extend along a straight line, wherein preferably the mounting section is arranged in the distal end of the shaft and also extends along the longitudinal direction. Therefore, in the mounted position of the retention element, the retention element is also aligned with the longitudinal axis of the dental tool. The retention element itself basically has a cylindrical shape (in particular its end portions), wherein the longitudinal axis of the cylinder corresponds with the longitudinal axis of the dental tool.

The mounting section is preferably constituted by a cavity arranged at the distal end of the shaft. The cavity is open to the distal end surface of the shaft (defining an entrance hole) such that an implant driver can be inserted into the mounting section along the longitudinal direction of the dental tool. In other words, the shaft has a cavity or opening arranged at the distal end surface of the shaft which is provided for inserting the implant driver into the shaft.

Additionally, at least one side opening is provided at the outer surface of the shaft at the distal end thereof. The side opening allows that fluid can flow through the side opening into the cavity of the mounting section. In particular, it is possible that fluid can flow through the side opening into the mounting section and out of the cavity or opening (i.e. through the entrance hole).

The side opening is arranged on the side surface of the shaft i.e. a surface extending along the circumferential direction and the longitudinal direction. The side opening constitutes a through-hole which is completely defined (surrounded) by the outer surface of the shaft. Thus, the most distal end of the shaft exhibits an annular portion which completely extends in the circumferential direction of the shaft. For example, the inner surface of this annular portion (which faces the inside of the cavity) may exhibit a surface (corresponding to a shaft drive portion) which provides an interlocking engagement with an implant driver such as a hexagonal inner surface. As such, the entrance hole for inserting the implant driver into the cavity is separated from the side opening by the outer surface of the shaft.

The retention element as referred to above may comprise two end portions and a narrower middle portion, wherein said middle portion and at least one of the end portions are hollow such that an implant driver may be received within the retention element. In a preferred embodiment, both end portions of the retention element are hollow such that cleaning and sterilization of the interior surfaces of the retention element may be further facilitated. The at least one hollow end portion is to be positioned at the distal end of the tool shaft when held in the tool, such that the retention element may hold the implant driver which shall protrude from the proximal end of the shaft.

The retention element may solely consist of the two end portions and the narrow middle portion. In particular, the middle portion connects the two end portion with each other; the middle portion is arranged between the two end portions. Preferably, the two end portions and the middle portion are a unitary component. The flexibility of the middle portion is preferably constituted by the shape and/or material of the middle portion. For example, the retention element has a reduced thickness at the middle portion which provides a greater elasticity compared to the end portions. Furthermore, the middle portion may be manufactured from an elastic material such as metal with reduced thickness. As such, the flexibility of the middle portion is provided by the characteristics of the middle portion alone such that further elements such as a spring are not needed. In particular, the middle portion is free of an additional spring.

The end portions of the retention elements may have the shape of a hollow cylinder, in particular a circular hollow cylinder. Therefore, fluid can flow through the end portions along the longitudinal direction. In particular, the retention element allows that fluid can flow along the longitudinal direction through the proximal end portion, the middle portion and the distal end portion. In general, the distal end portion and the proximal end portion provide a first opening and a second opening. The first opening is provided in order that the implant driver can be inserted into the retention element. The second opening may also be used for accommodating the implant driver but also to enhance the flow of fluid for improving the cleaning of the retention element.

The end portions of the retention element may be compressible such that when the retention element is inserted into the shaft of the tool, in particular in the mounting section of the tool, it may be held in place due to friction, as the end portions of the retention element may have a larger diameter than the internal diameter of the shaft.

The middle and narrower portion of the retention element may be flexible and somewhat radially expandable such that insertion of an implant driver pushes the middle portion of the retention element outwards, and the implant driver may be held inside the retention element via friction. Much like the relationship between the end portions of the retention element and the shaft, the narrow middle portion of the retention element may have a smaller internal radius than the shaft radius of the implant driver, thus leading to said friction of it.

As an object of the present invention is for the tool to be easily cleaned, it is generally preferred that the retention element comprises a number of slits or retention openings such that water or a cleaning fluid may easily be passed from the outside of the narrow portion to the inside of the retention element. These retention openings may extend longitudinally along the retention element. It is thus preferable that the retention openings in the retention element are equally spaced apart when positioned around the narrow portion of the retention element, and differ in number to the side openings of the shaft.

It is further preferable that the retention openings of the retention element and the side openings of the shaft are not a multiple or a factor of one another, such that when the retention element is held in the shaft, it can be ensured that regardless of orientation of the retention element, solid portions of the middle section of the retention element do not block all of the side openings of the shaft. This thus allows it to be ensured that cleaning fluid may be passed from the outside of the shaft to the inside of the shaft via the retention element.

Most preferably, the retention element comprises four retention openings spaced around the narrow middle section, whilst the shaft (mounting section) comprises three side openings spaced around the mounting section.

It is also preferred that the at least one side opening of the mounting section extends further along the shaft than the proximal end portion of the retention element (i.e. the end portion which penetrates furthest into the shaft) such that cleaning fluid may be passed through the mounting section openings or side openings directly into the shaft, above the end portion of the retention element when said retention element is held inside the shaft. This further ensures that cleaning fluid may be passed into the distal end of the shaft.

Furthermore, the handle of the dental tool may comprise a cap, or may have a separate cap attached to the handle. Said cap may comprise a blind hole or cap cavity wherein the internal geometry of said blind hole reflects the internal geometry of an implant, including for example anti-rotational features and threading. The internal geometry of the cap thus allows an abutment which is designed to be held in said implant which the internal geometry is analogous to, may be held in the cap due to the external geometry of the abutment being designed to mate with the internal geometry of the implant. A screw may also be used to pass through an abutment and interact with threads in the blind hole.

The proximal circumference of the blind hole, i.e. the edge of said hole on the outer surface of the cap may be shaped such that it has the same cross-sectional shape as the shoulder of the implant of which it is the analog.

When the cap is designed to hold an abutment in the blind hole and comprise a circumferential shape identical to that of the implant shoulder, the abutment may fit neatly to the blind hole. This further provides the possibility to attach an abutment or abutment analog on which a crown can be placed such that said crown may have adjustments made whilst held on the abutment or abutment analog.

In addition, an abutment or a healing abutment may also be adjusted manually in this holding position in the blind hole. Furthermore, such modified (individualized) crowns or (healing) abutments may be scanned with, for example, an intraoral scanner. The scanned image may thus be used to subsequently manufacture the individualized shape, for example for a permanent crown or abutment or a crown or abutment made of another material Alternatively, the blind hole of the cap may have an internal surface adapted to hold dental instruments such as the implant driver or screw driver.

The cap may also comprise one or more channels which connect an outer surface of the cap to the bottom of the blind hole. This thus allows cleaning fluid to be passed through said channels and clean the blind hole of the cap more efficiently.

The cap may be attached to the handle via complementary threads on an external surface of the cap and an internal surface of the handle (or vice versa). Alternatively, the cap is fixed to the handle in a permanent way, for example via an adhesive and/or through a laser welding procedure.

It is also preferable that an external surface of the cap comprises one or more (most preferably six) markings. Said markings may provide the user with information, for example directing the user to the blind hole. Alternatively, said markings may provide the user with an indication of the internal geometry of the blind hole within the cap such that the orientation is known in which the abutment or dental instrument is held in the blind hole, which orientation corresponds to the orientation in the implant. The markings may also be useful when scanning the (healing) abutment or crown.

It is further preferable that the shaft of the dental tool comprises a portion around the circumference of the shaft wherein a ratcheting device may be engaged. Said portion may form an interface between the shaft and said ratcheting device by comprising a plurality of grooves designed to contact teeth of the ratcheting device such that a rotational force applied to the ratcheting device in one direction may be transferred to a rotational force on the dental tool. These grooves may extend longitudinally along the shaft whilst being spaced around the circumference of said shaft.

The invention may be defined by the following aspects:

1. A tool (100, 200) for use in dental implant treatments, comprising:
   a handle (102, 202);
   a shaft (103, 203) connected to the handle (102, 202), wherein the shaft (103, 203) comprises a mounting section on the distal end;
   the mounting section comprising at least one opening at the distal end of the shaft (103, 203), extending along the shaft (103, 203);
   a retention element (104, 204) held inside the mounting section of the shaft (103, 203) for holding an implant driver (110, 300).

2. The tool (100, 200) of aspect 1, wherein the retention element (104, 204) has two end portions (2041, 2043) and a middle portion narrower than the end portions (2041, 2043), wherein the middle portion and at least one of the end portions (2041, 2043) are hollow, wherein preferably both end portions (2041, 2043) are hollow.

3. The tool (100, 200) of aspect 2, wherein the end portions (2041, 2043) of the retention element (104, 204) are radially compressible and the inner cross section of the mounting section of the shaft (103, 203) is narrower in diameter than the end portions (2041, 2043), such that the retention element (104, 204) is held in the mounting section due to friction at both end portions (2041, 2043), wherein preferably the at least one opening of the mounting section extends further along the shaft (103, 203) than the proximal end portion of the retention element (104, 204) when the retention element (104, 204) is held in the shaft (103, 203).

4. The tool (100, 200) of aspects 2 or 3, wherein the middle portion of the retention element (104, 204) is flexible and may be pushed outwards by an implant driver (110, 300) with a wider diameter, thereby holding the implant driver (110, 300) in place due to friction.

5. The tool (100, 200) of any of the preceding aspects, wherein the retention element (104, 204) comprises one or more openings in the external surface of the middle potion, wherein preferably the number of openings in the retention element (104, 204) differs from the number of side openings in the mounting section, further preferably the retention element (104, 204) comprising four openings and the mounting section comprises three openings.

6. A retention element (104, 204) for holding an implant driver (110, 300), in particular for use in a tool (100, 200) according to one of aspects 1 to 5, comprising:
   two end portions (2041, 2043), wherein one or both end portions (2041, 2043) are hollow;
   a hollow middle portion;
   wherein the middle portion is narrower than the end portions (2041, 2043);
   and the middle portion is radially flexible.

7. The retention element (104, 204) of aspect 6, wherein the end portions (2041, 2043) are radially compressible.

8. The retention element (104, 204) of either aspect 6 or 7, wherein the middle portion may be pushed outwards by insertion of an implant driver (110, 300) with a wider diameter.

9. The retention element (104, 204) of any of aspects 6-8, wherein the retention element (104, 204) comprises one or more openings in the external surface of the middle portion.

10. A tool (100, 200) for use in dental implant treatments, comprising:
    a handle (102, 202);
    a shaft (103, 203) connected to the handle (102, 202) with an opening in the distal end for holding an implant driver (110, 300);
    characterized in that:
    the handle (102, 202) is connected to a cap (101, 201), wherein the cap (101, 201) comprises a blind hole (1011) with an internal geometry analogous to an internal geometry of an implant for holding an abutment or other dental instruments.

11. The tool (100, 200) of aspect 10, wherein the proximal circumference of the blind hole (1011) has the shape of an implant shoulder.

12. The tool (100, 200) of aspects 10 or 11, wherein the cap (101, 201) comprises one or more channels (1012) from the surface of the cap (101, 201) to the bottom of the blind hole (1011).

13. The tool (100, 200) of any of aspects 10-12, wherein the cap (101, 201) is fixed to the handle (102, 202) by an adhesive or by laser welding.

14. The tool (100, 200) of any of aspects 10-13, wherein the cap (101, 201) comprises one or more markings (1015), which convey information to the user regarding the blind hole (1011).

15. A tool (100, 200) for use in dental implant treatments, comprising:
    a handle (102, 202);
    a shaft (103, 203) connected to the handle (102, 202) with an opening in the distal end for holding an implant driver (110, 300);
    characterized in that:

the shaft (103, 203) comprises an interface portion (1031, 2031) extending around the circumference of the shaft (103, 203) for engagement with a ratcheting device;
wherein the interface portion (1031, 2031) is located around the proximal end of the shaft (103, 203), wherein the proximal end is the end connected to the handle (102, 202).

16. The tool (100, 200) of aspect 15, wherein the interface portion (1031, 2031) comprises a plurality of grooves, wherein the grooves extend longitudinally along the shaft (103, 203).

BRIEF DESCRIPTION OF FIGURES

FIG. 12A shows a side view of a handle driver according to the present invention wherein said handle driver is holding an implant driver being adapted for use with a ratchet.

FIG. 12B provides a cross-sectional side view of part of the cap along axis a-a as seen in FIG. 12A.

FIGS. 15A and 15B provide views of the shaft of a handle driver embodiment.

FIG. 15C provides a cross-sectional view of the mounting portion of the distal end of the shaft along axis A-A as indicated in FIG. 15B.

FIG. 16A provides a cross-sectional view of an embodiment of the handle driver according to the present invention.

FIG. 16B provides a magnification of a part of the mounting portion of the handle driver seen in FIG. 16A with a retention element of FIG. 8.

DETAILED DESCRIPTION OF EMBODIMENTS

Figures 1A, 1B:
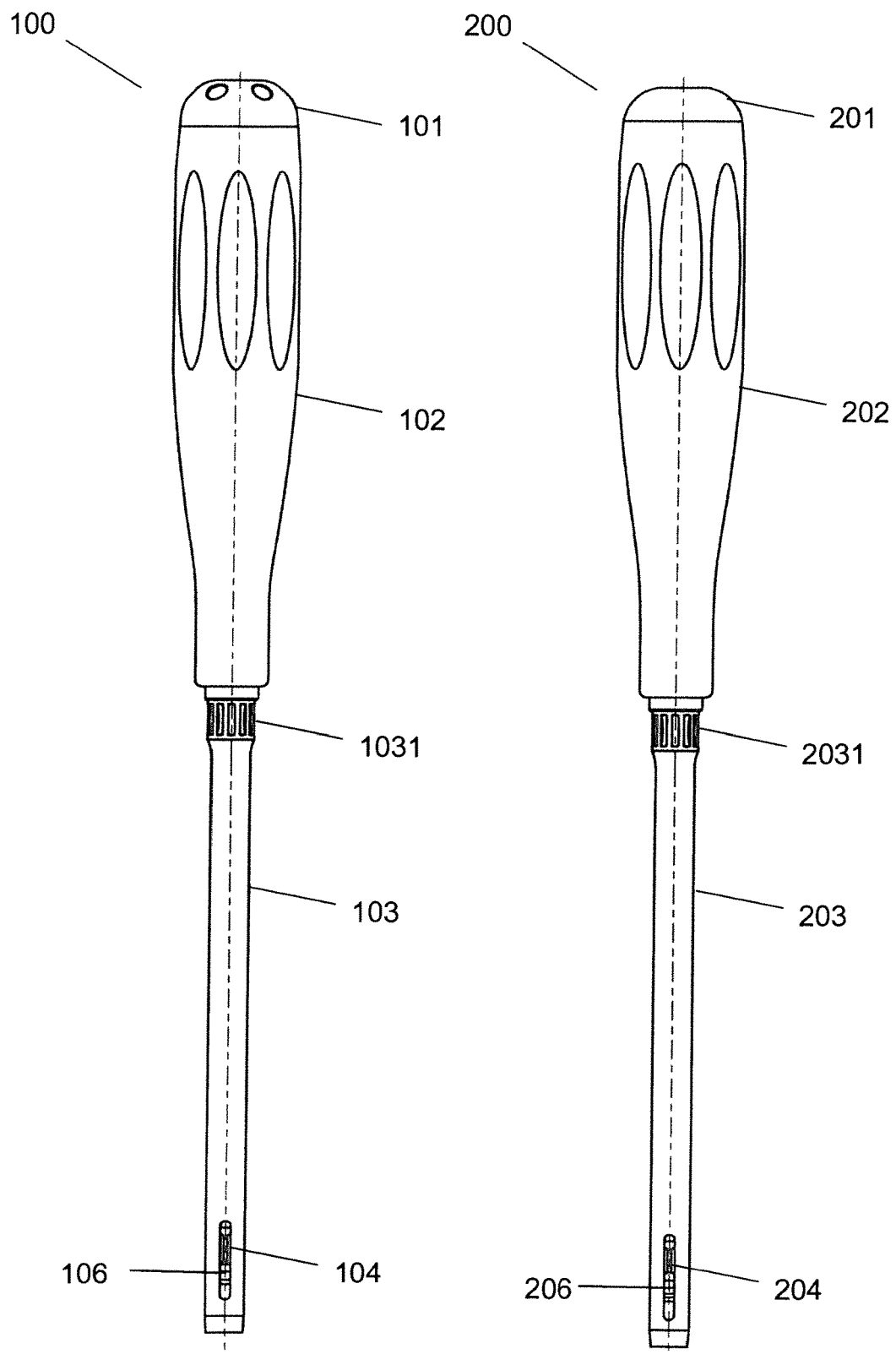
FIG. 1A provides a side view of a dental tool according to an embodiment of the present invention.
FIG. 1B relates to another embodiment of the present invention comprising a handle driver.

FIG. 1A provides a side view of a dental tool according to an embodiment of the present invention. Dental tool 100 may be considered a screwdriver or handle driver and thus may be referred to as such herein.

Said handle driver 100 comprises a cap 101 affixed to a handle 102 which may comprise a plurality of grip portions for increased grip for the user when held. Said handle 102 should have a length that allows for it to be held in a human hand such that the handle driver 100 may be operated manually. Said cap 101 may be referred to as forming part of the proximal end of the handle driver 100, positioned on the end of the handle 102 opposite to the end connected to a shaft 103. Said cap 101 may be substantially dome shaped.

Said shaft 103 may extend into the handle 102 and be secured to the inside of said handle 102. The upper portion of the shaft 103, i.e. the end connected to the handle 102 may also comprise an interface portion 1031 around the circumference of the shaft 103. Said interface portion 1031 may not extend into the handle 102, but should be exposed such that it may interact with a ratcheting device. Said interface portion 1031 may comprise a plurality of grooves extending from the proximal end 109 of the shaft 103 (the end connected to the handle 102) towards the distal end of the shaft 103. Said shaft 103 may extend longitudinally away from the handle 102 and may have a rotationally symmetrical cross section, preferably circular or hexagonal.

At the distal end of the shaft 103, an opening or cavity 112, 212 is present which extends from the most distal end surface into, and through, the shaft 103 such that the shaft is hollow for at least a portion of the way through the shaft 103.

The distal end of the shaft 103 may also comprise at least one, preferably three, side openings 106, 206 which are formed in the outer surface of the distal end of the shaft 103 in what is herein referred to as a mounting section.

Said side opening/openings 106, 206 extend longitudinally along the shaft 103 in the mounting section and can facilitate the passing of fluid from outside the handle driver 100 to the inside of the shaft 103. Said side openings 106, 206 may be oval or rectangular in shape.

The handle driver 100 may comprise a retention element 104 held in the mounting section of the shaft 103. Said retention element 104 may be held in the handle driver 100 via a frictional fit. Said retention element 104 may be permanently fixed or may be removable when necessary.

FIG. 1B relates to another embodiment of the present invention comprising a handle driver 200. Unless stated otherwise, it is considered that the handle driver 200 of this embodiment comprises substantially identical features to the handle driver 100 of the first embodiment.

Figures 2A, 2B:
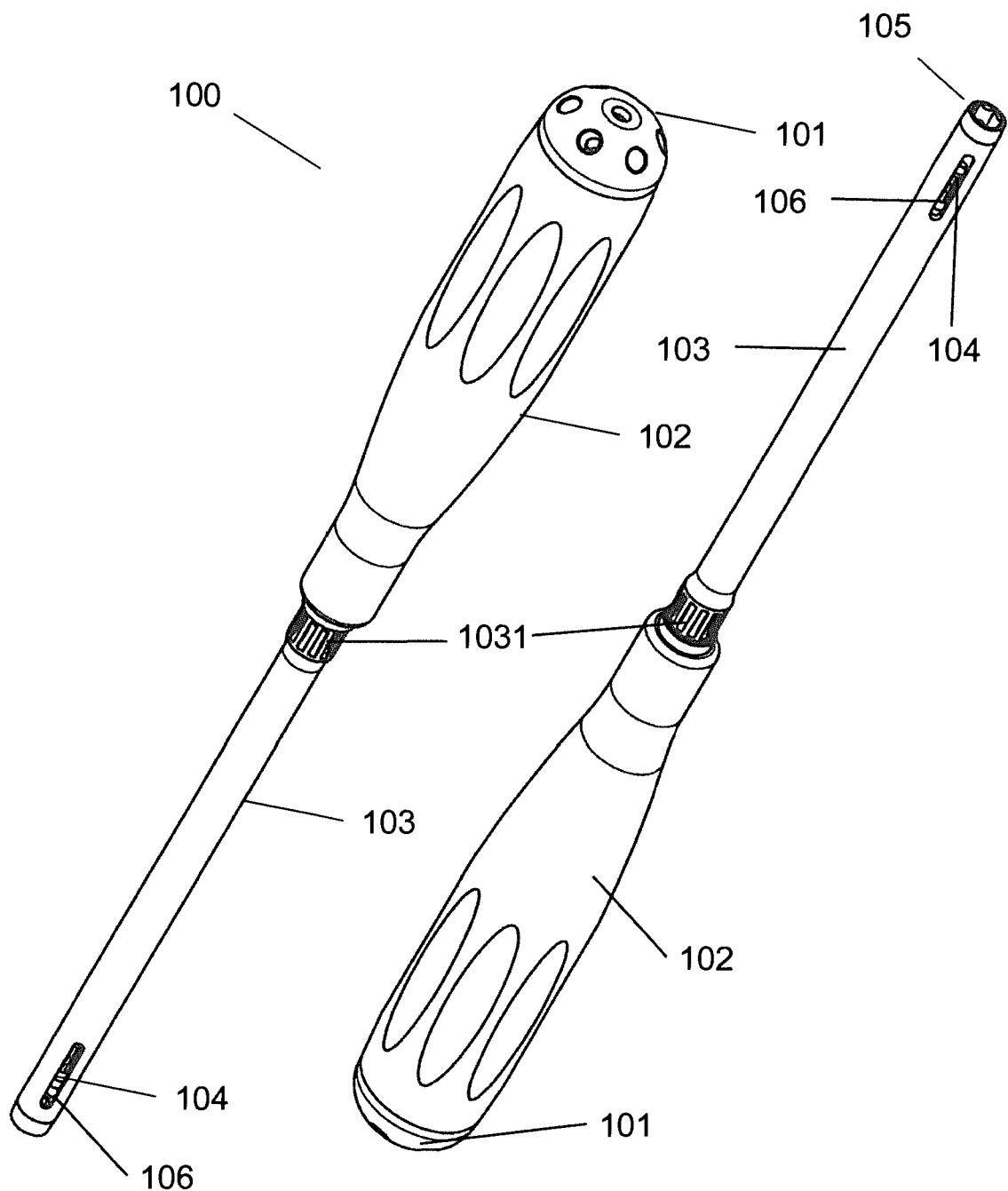
FIGS. 2A and 2B provide an alternate viewing angle of a handle driver according to the embodiment of the present invention seen in FIG. 1A.

FIGS. 2A and 2B provide an alternate viewing angle of a handle driver 100 according to the embodiment of the present invention seen in FIG. 1A. It can be seen that the distal end surface cavity may have a preferably hexagonal cross-section constituting a shaft drive portion 105. Said cross section may also be elliptical, octagonal, or of any alternative cross-section which would allow for transmitting torque to the implant driver.

Figures 3A, 3B:
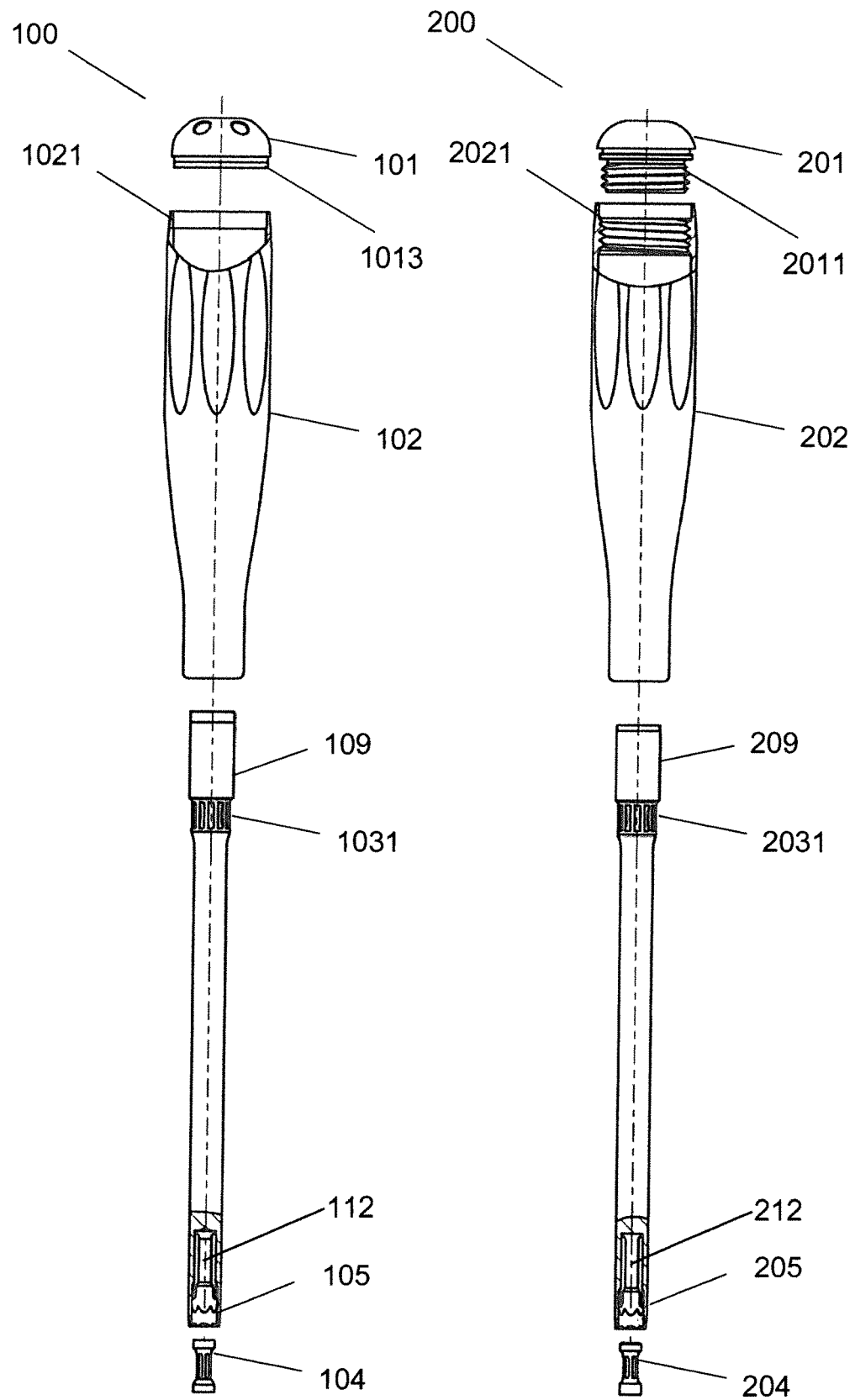
FIGS. 3A and 3B provide an exploded (and partially cut away) side view of the embodiments of FIGS. 1A and 1B respectively.

FIGS. 3A and 3B provide an exploded (and partially cut away) side view of the embodiments of FIGS. 1A and 1B respectively. Said view provides a clearer look at the proximal end 109, 209 of the shaft 103, 203 which when assembled is held inside the handle 102, 202. Furthermore, the retention element 104, 204 may be seen prior to its instalment in the mounting section of the shaft 103, 203 and a substantially cut away view of the mounting section provides a clearer image as to the internal surface structure of the mounting section including the shaft drive portion 105/205. It can also be seen that the embodiments have different features regarding the cap 101, 201 and handle 102, 202 and how said features are fixed together (these shall be discussed in more detail regarding FIGS. 9 and 10, specifically related to the cap 101, 201 and handle 102, 202).

Figures 4A, 4B:
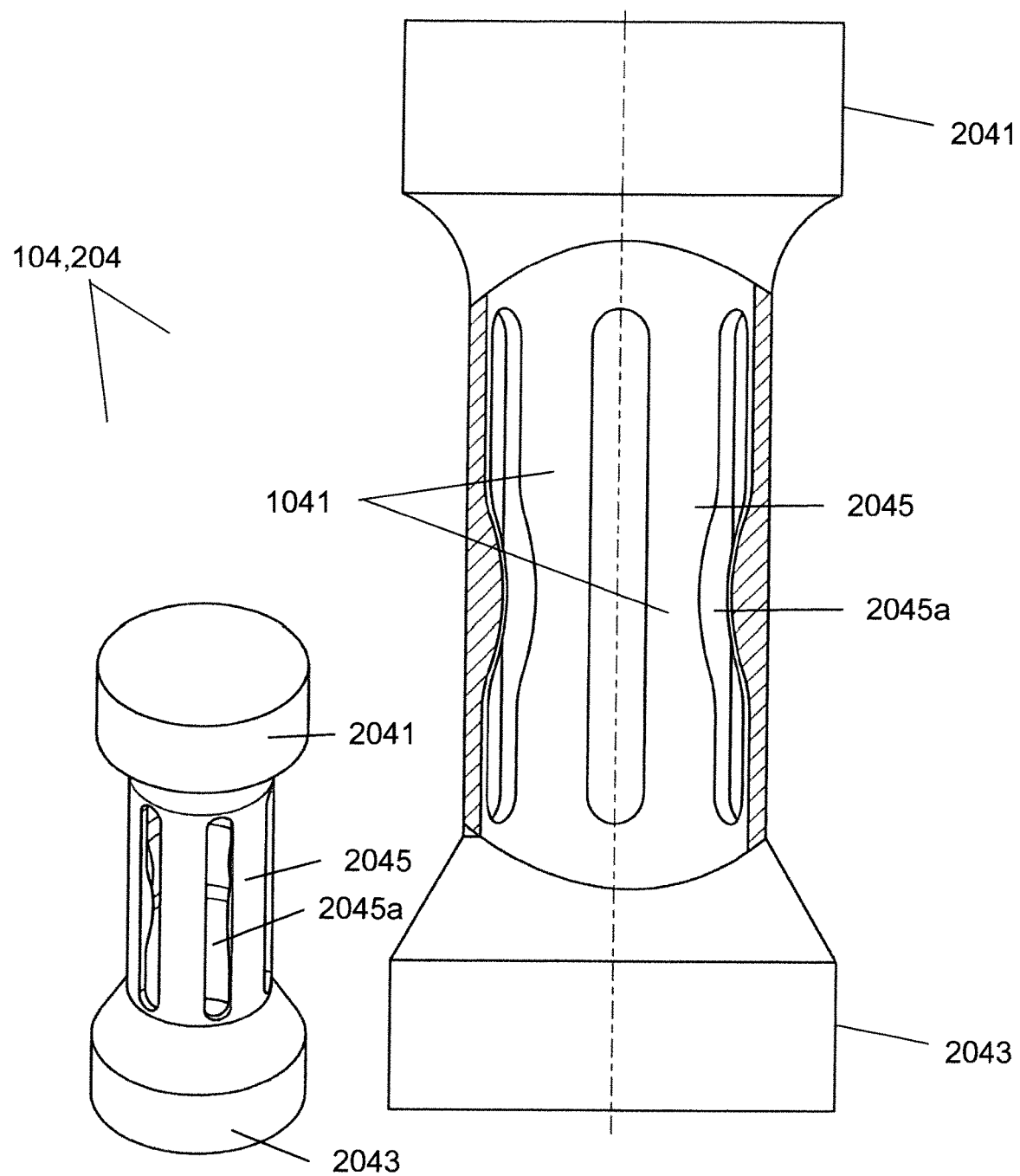
FIG. 4A shows an elevated view of a retention element according to the present invention.
FIG. 4B shows the retention element of FIG. 4A from a side view (and partially cut away).

FIG. 4A shows an elevated view of a retention element 104, 204 according to the present invention, whilst FIG. 4B shows the retention element 104, 204 from a side view. It may clearly be seen that the retention element 104, 204 comprises two end portions (a proximal end portion 2041 and distal end portion 2043) and a middle portion 2045. The end portions 2041, 2043 may be cylindrical, as this aids in ensuring a uniform press fit when inserted into the mounting section of a handle driver 100, 200. Said middle portion 2045 is narrower (i.e. has a smaller diameter) than the end portions 2041, 2043. Said middle portion 2045 has a curved internal surface that is narrowest at the centre of the middle portion 2045. The diameter of said narrowest part may be less than the diameter of an implant driver shaft, to ensure that the implant driver shaft is held via a frictional fit.

Said middle portion 2045 may also comprise a plurality of retention openings 2045a extending along the side of the middle portion 2045 such that fluid may pass through the outer surface of the middle portion 2045 and into the inside of the retention element 104, 204. The retention openings 2045a aid in the flexible properties of the retention element 104, 204 and allow for expansion and retraction when implant drivers are pressed into the retention element 104, 204.

Distal end portion 2043 also comprises a first opening (not visible in the figures) such that the shaft of an implant driver (i.e. the portion that is usually held by a user with a dental handpiece) may be pushed through the first opening and pressed inside the retention element 104, 204. It is also preferred that the proximal end portion 2041 also has an second opening 2041a (see FIG. 8) such that it may further facilitate the cleaning and sterilization procedure of either the retention element 104, 204 or the handle driver shaft 103, 203 it is installed in. This may be the case for any of the following embodiments showing a retention element 104, 204.

Figures 5A, 5B:
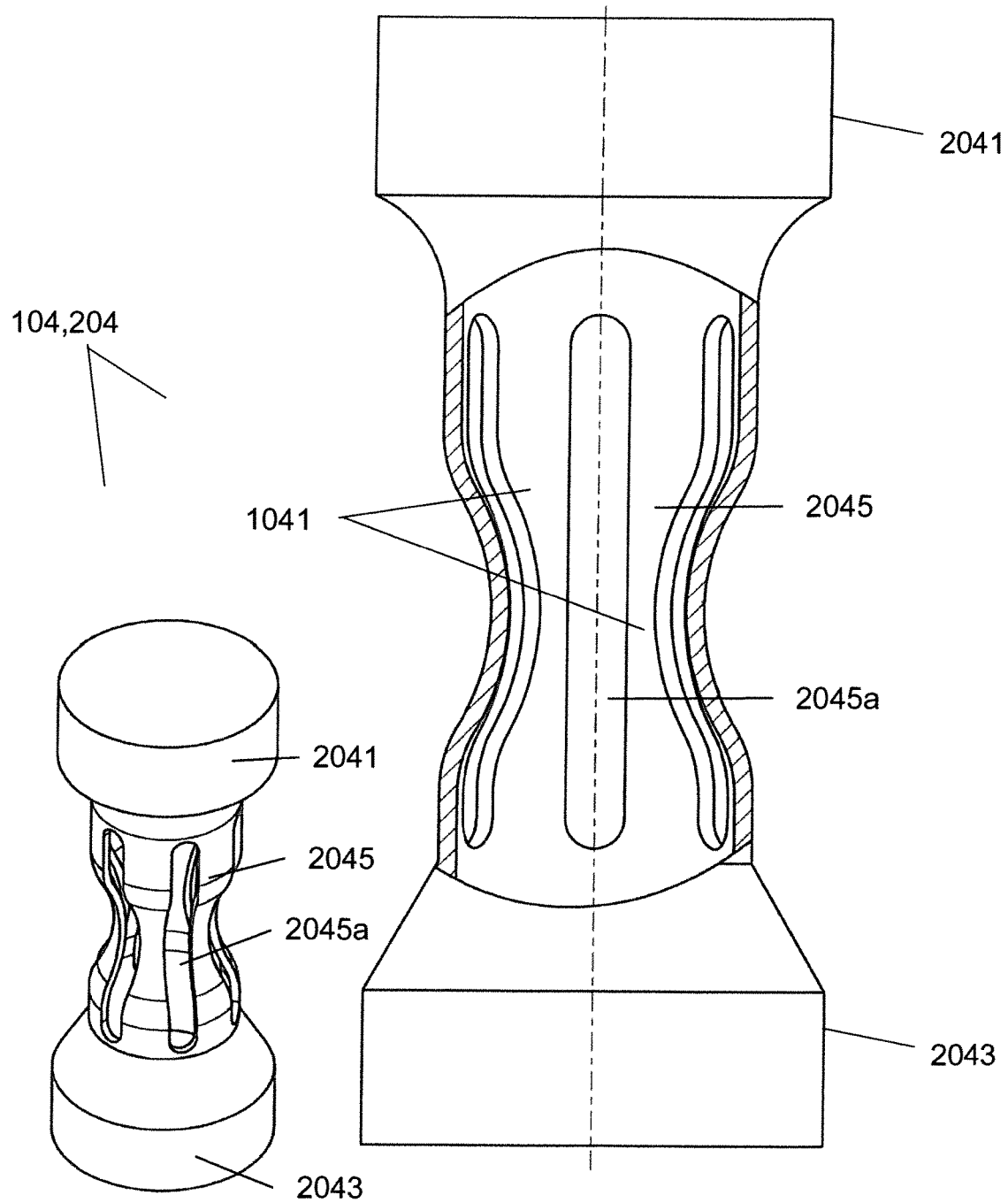
FIGS. 5A and 5B provide an elevated, and side view (and partially cut away) respectively of an alternative retention element shown, where a deformation step within a manufacturing process created the constriction.

FIGS. 5A and 5B provide an elevated, and side view respectively of a retention element 104, 204 according to the present invention, after a deformation step of a manufacturing process. During said deformation step, the middle portion 2045 is deformed such that it comprises inwardly curved surfaces of the retention element 104, 204. Said deformation step may comprise removal of material around the middle portion 2045 of the retention element 104, 204. Due to the achieved shape of the retention element 104, 204 with bent single elements, the friction can be increased with regard to a component to be inserted.

Figures 6A, 6B:
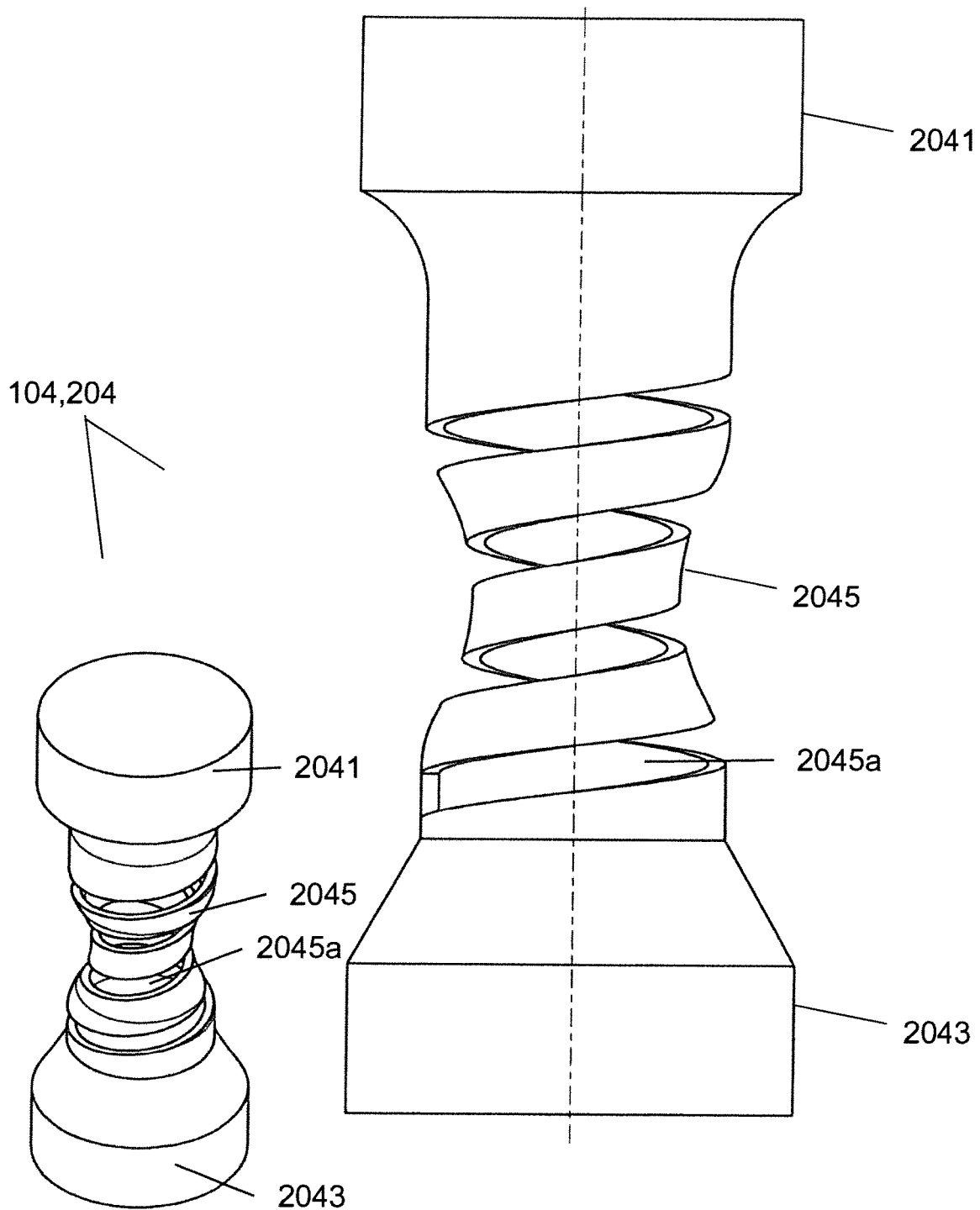
FIGS. 6A and 6B provide an elevated and side view respectively of an alternative retention element according to the present invention.

FIGS. 6A and 6B provide an elevated and side view respectively of an alternative retention element 104, 204 according to the present invention. The retention element 104, 204 of FIGS. 6A and 6B comprises a somewhat spring-shaped middle portion 2045 wherein the outer surface of the middle portion 2045 forms a spiral around the central axis extending from the proximal end portion 2041 to the distal end portion 2043.

Figures 7A, 7B:
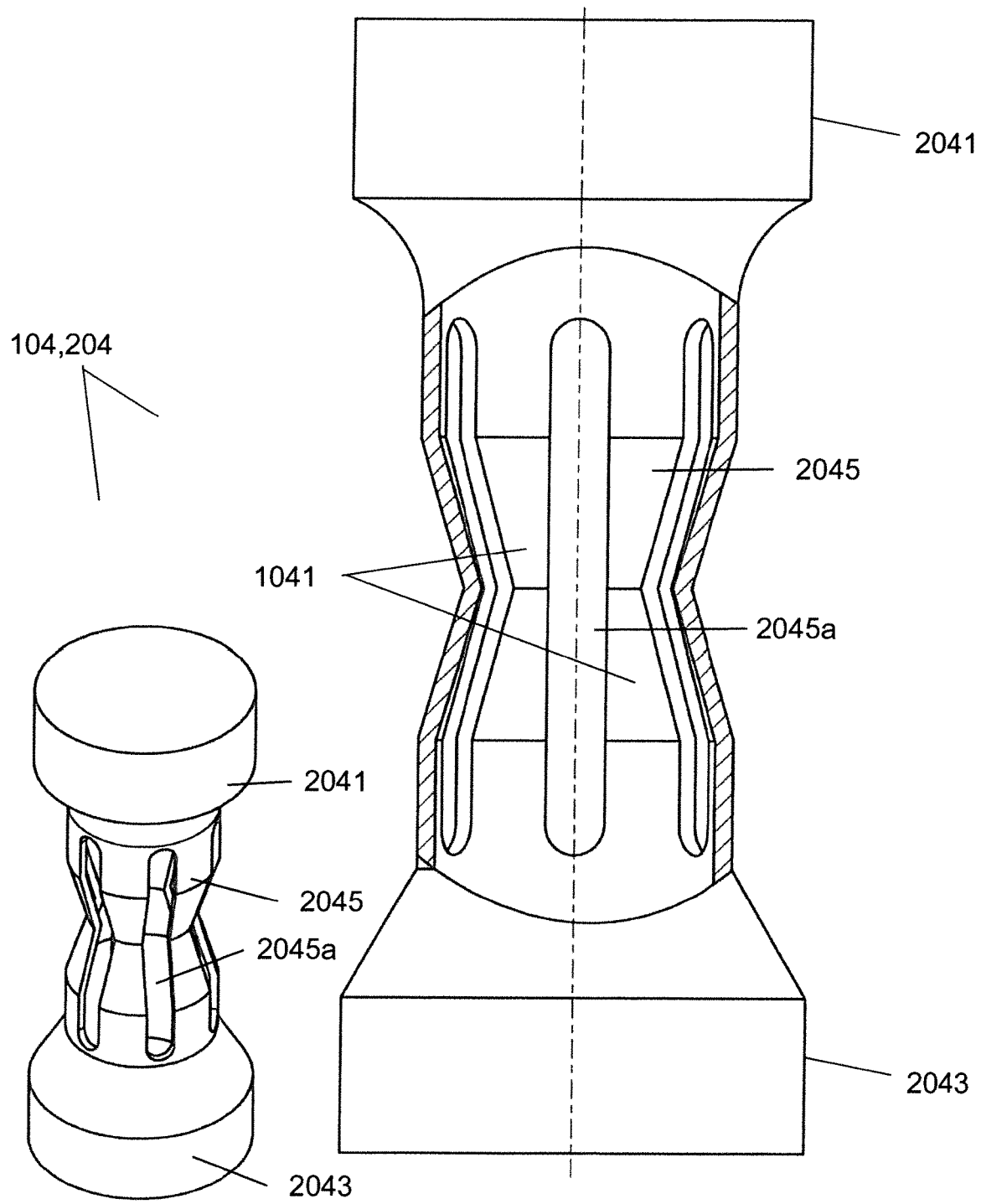
FIGS. 7A and 7B provide an elevated and side view (and partially cut away) respectively of a further embodiment of the retention element.

FIGS. 7A and 7B provide an elevated and side view respectively of a further embodiment of the retention element 104, 204. The retention element 104, 204 of FIGS. 7A and 7B differs from that of FIGS. 5A and 5B in that the middle portion 2045 has a non-curved outer surface that narrows when it approaches the middle of the retention element 104, 204. Due to the individual elements of the middle portion 2045, each of which has an inwardly directed edge, friction with respect to an element to be introduced is again increased.

Figure 8:
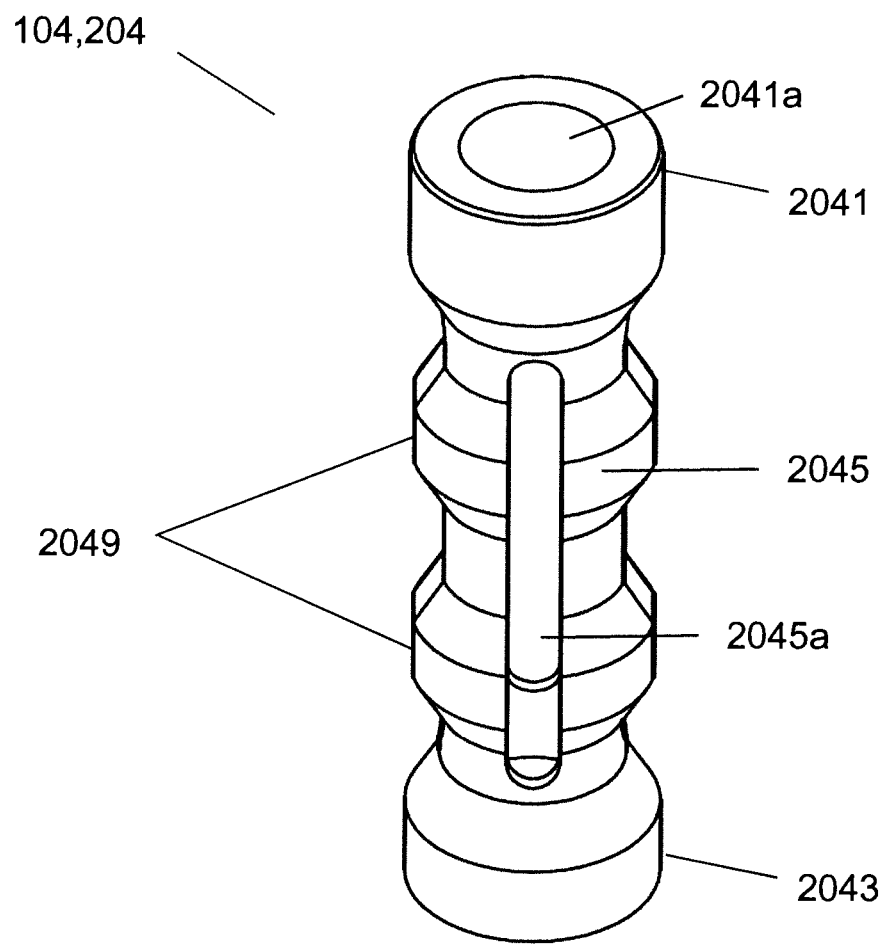
FIG. 8 provides an elevated view of a further retention element according to the present invention.

FIG. 8 provides an elevated view of a further retention element 104, 204 according to the present invention, wherein said element has multiple narrow portions of the retention element's middle portion 2045, preferably three narrow portions. The middle portion 2045 thus also comprises multiple, preferably two, wider sections 2049 which have a diameter preferably up to 0.25 mm, more preferably between 0.05 and 0.20 mm, more preferably up to 0.18 mm and most preferably between 0.15 and 0.1 mm less than the proximal end portion 2041 of the retention element 104, 204. These provide a more robust system which can grip an implant driver shaft in any of the narrow portions and in addition the wider sections 2049 may be compressible such that they aid in the press fit of the retention element 104, 204 in the shaft 103, 203. In this example, the middle portion 2045 has four flexible connecting strips 1041. Due to the widening, the flexible connecting strips 1041 are not permanently bent or overstretched if an implant driver shaft is inserted with a slight cant.

Figure 9A:
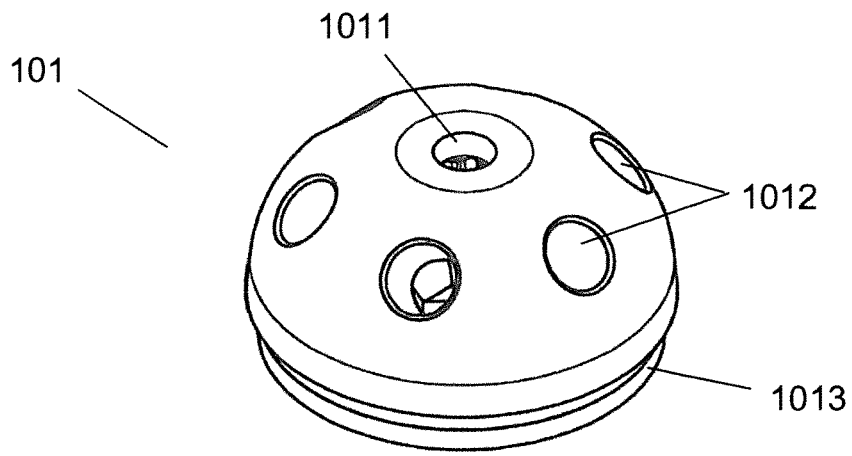
FIGS. 9A, 9B and 9C provide an elevated view, bird's eye view and cross-sectional side view respectively, of a cap according to the present invention.
Figure 9B:
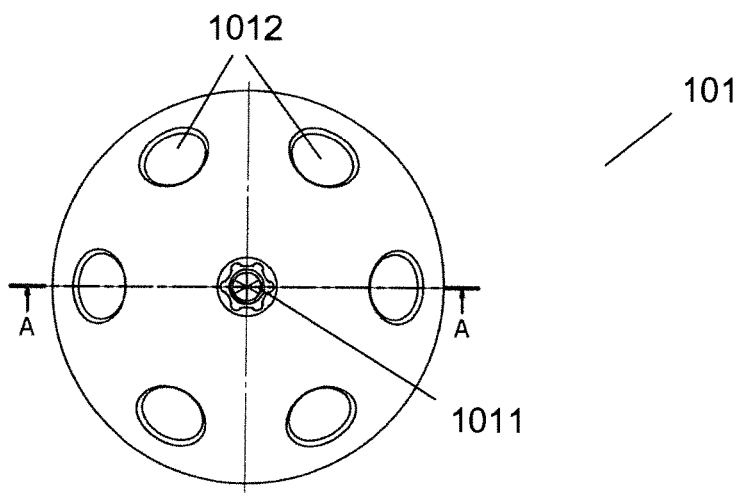
Figure 9C:
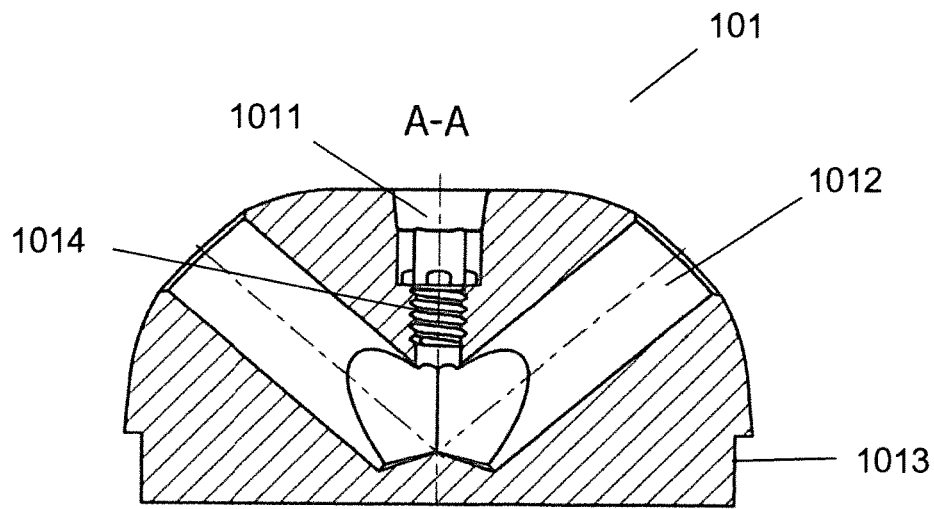

FIGS. 9A, 9B and 9C provide an elevated view, bird's eye view and cross-sectional side view respectively, of a cap 101 according to the present invention. FIG. 9C is a cross sectional view along the axis A-A of FIG. 9B. The cap 101 may comprise a blind hole 1011 or cap cavity in the top (preferably centre) of the cap 101. Said blind hole 1011 or cap cavity has an internal surface geometry, preferably reflecting the internal geometry of an implant, suitable for the holding of dental instruments or prosthetic parts.

As can be seen most clearly in FIG. 9C, the blind hole 1011 or cap cavity has a wider upper section and a narrower threaded lower section 1014. Said cap 101 may also comprise a plurality of channels 1012 in the outer surface of the top, which penetrates to the base of the lower portion of the cavity where the channels 1012 meet, directly below the cavity opening. Said channels 1012 render cleaning and sterilization operations far easier as there are multiple entrances and exits for fluid to pass through during cleaning and sterilization operation. The cap 101 also comprises an insert portion 1013 which is adapted to be inserted into the top of the handle 102. Said cap 101 may be press fit into the handle 102, laser welded to the handle 102, attached via adhesive, or via any standard fixing means.

Figure 10A:
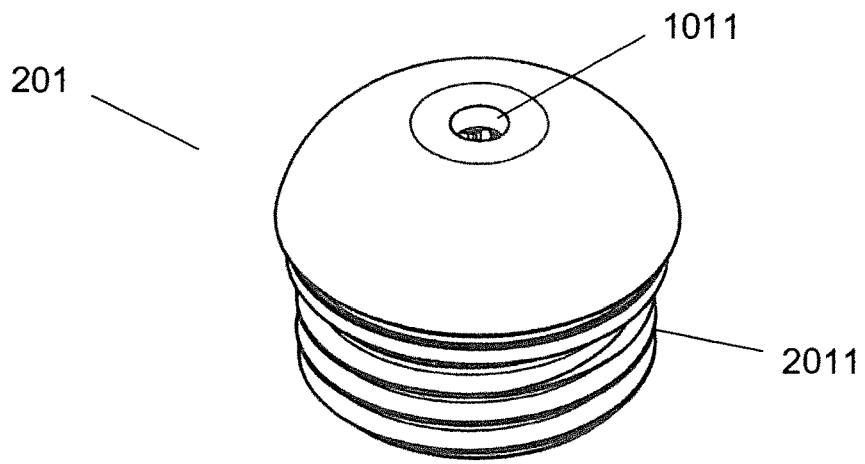
FIGS. 10A, 10B and 10C provide an elevated view, bird's eye view, and cross-sectional side view respectively of another cap according to the present invention.
Figure 10B:
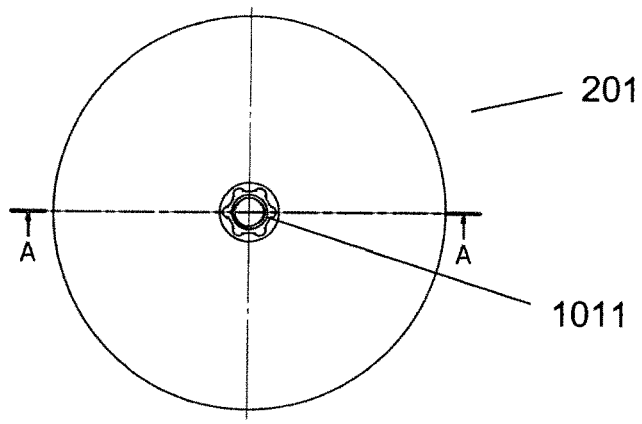
Figure 10C:
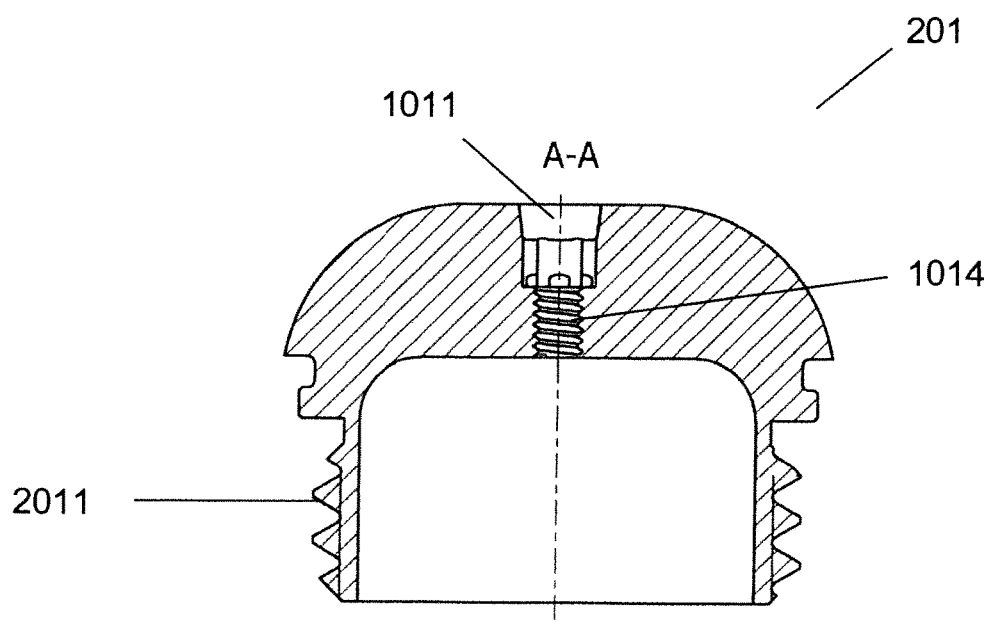

FIGS. 10A, 10B and 10C provide an elevated view, bird's eye view, and cross-sectional side view respectfully of another cap 201 according to the present invention. FIG. 10C is a cross sectional view along the axis A-A of FIG. 10B. Said cap 201 however is adapted to be connected with the handle 202 of the handle driver 200 via a screw thread 2011 on the outer surface of the cap 201. Said screw thread 2011 is designed to allow the cap 201 to be screwed into an opening of the upper portion of the handle 202 comprising a complementary internal thread 2021. Whilst not pictured in FIGS. 10A-10C, the cap 201 may also comprise one or more channels 1012.

Figure 11A:
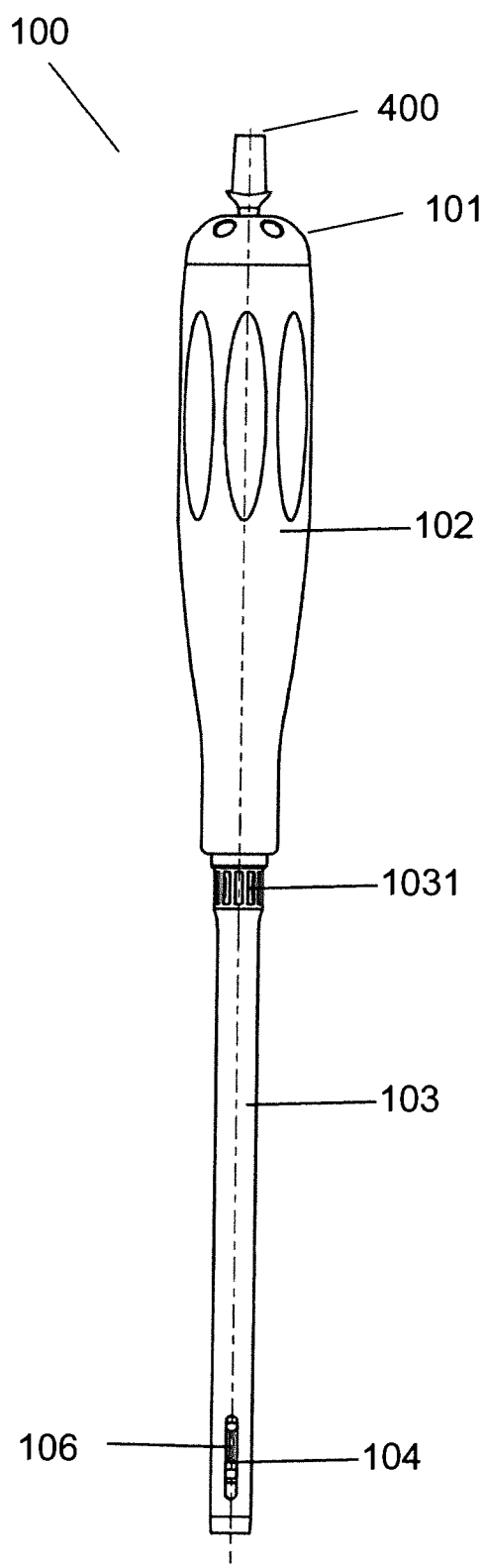
FIG. 11A shows a side view of a handle driver according to the present invention wherein said handle driver is holding an abutment.
Figure 11B:
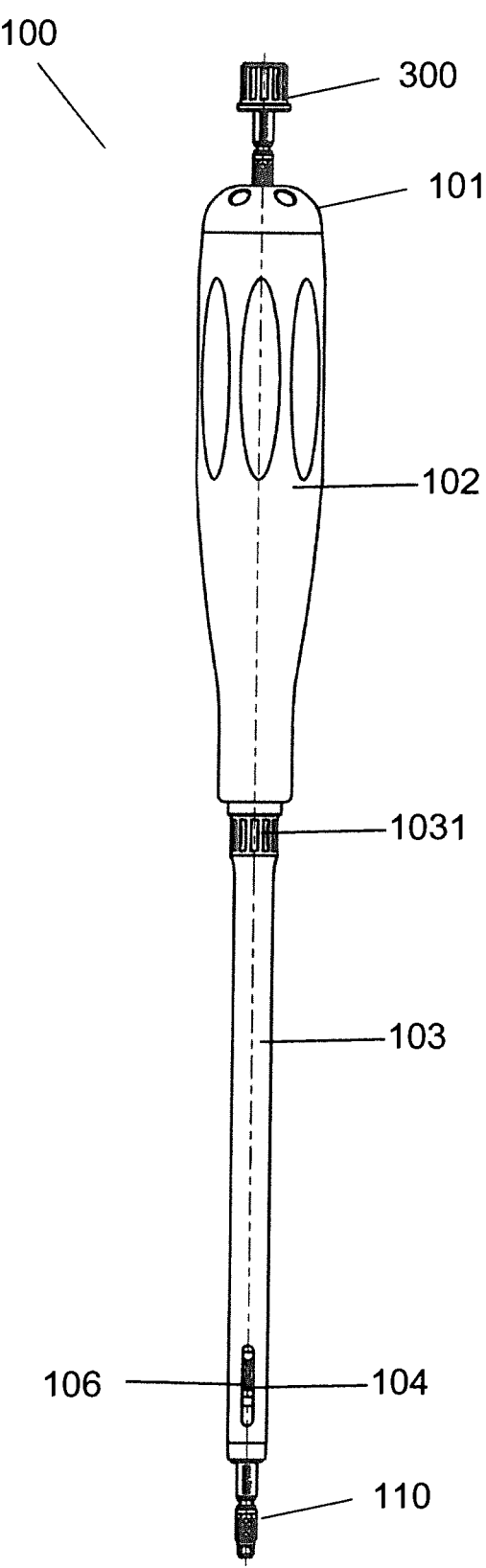
FIG. 11B shows a side view of a handle driver according to the present invention wherein said handle driver is holding two implant drivers, one being adapted for use with a ratchet.

FIGS. 11A and 11B show a side view of a handle driver 100 according to the present invention (preferably the embodiment outlined in FIG. 1A), wherein in FIG. 11A an abutment 400 or abutment analog 400 (an abutment replica which has a similar surface shape such that it may hold a crown) and in FIG. 11B said handle driver 100 is holding an implant driver 300 adapted for use with a ratchet, both of which are held in the blind hole 1011 of the cap 101 as previously outlined. In addition, FIG. 11B shows an implant driver 110 inserted into the distal end of the shaft 103.

FIG. 12A shows a side view of a handle driver 100, 200 according to the present invention wherein said handle driver 100, 200 is holding an implant driver 300 adapted for use with a ratchet.

FIG. 12B provides a cross-sectional side view of part of the cap 101 along axis A-A as seen in FIG. 12A. Said cross-sectional view of FIG. 12B shows how the implant driver 300 adapted for use with a ratchet may fit into the upper part of the blind hole 1011 of the cap 101 and be held in place so that torque may be transmitted via the distal end of the shaft 103, 203 to the implant driver 110 when a ratchet is attached to the head 301.

Figures 13A, 13B:
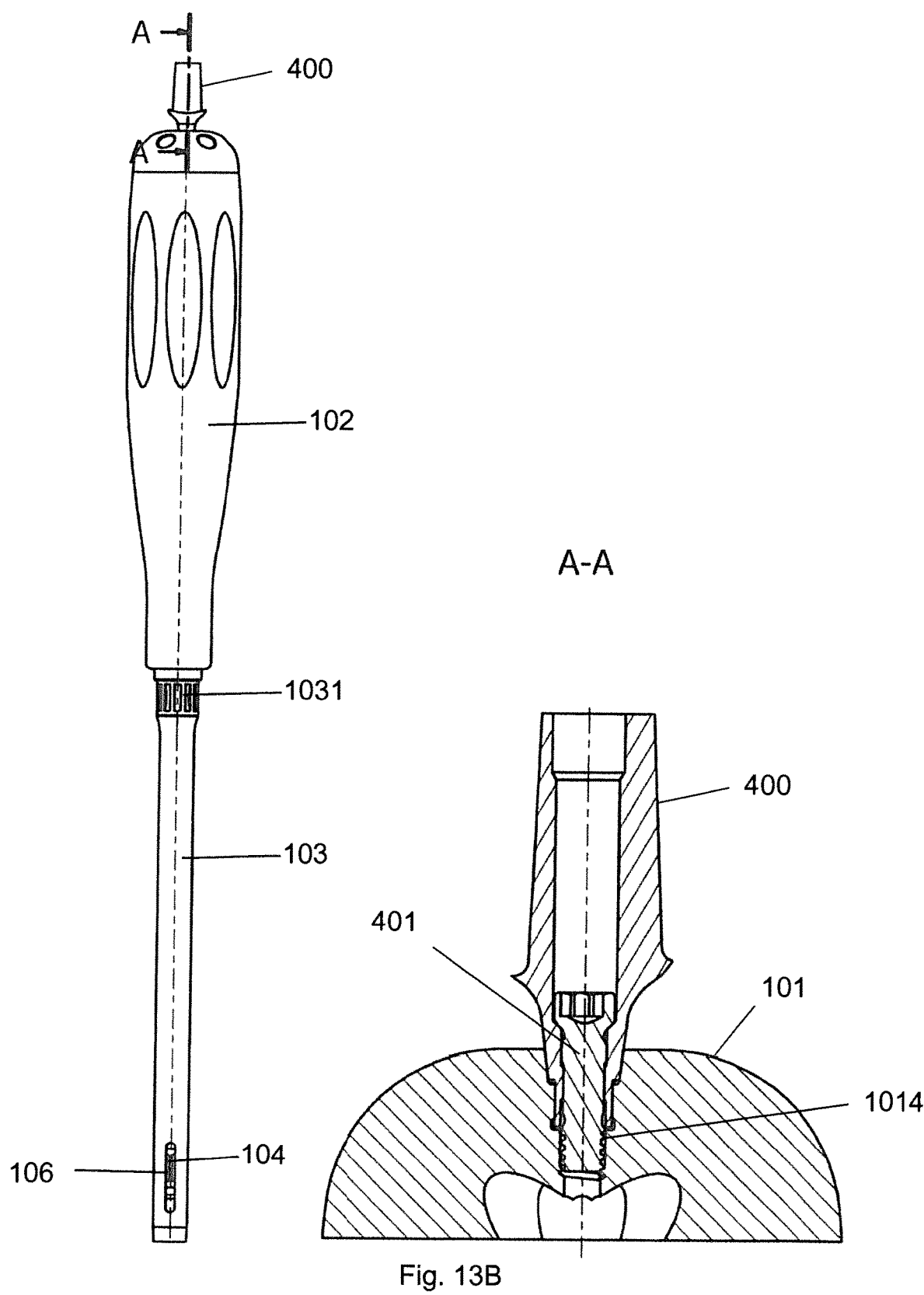
FIG. 13A shows a side view of a handle driver according to the present invention wherein said handle driver is holding an abutment or abutment analog.
FIG. 13B provides a cross-sectional view of at least part of the cap as shown along axes a-a as seen in FIG. 13A.

FIG. 13A shows a side view of a handle driver 100, 200 according to the present invention wherein said handle driver 100, 200 is holding an abutment 400 or abutment analog 400. FIG. 13B provides a cross-sectional view of at least part of the cap 101 as shown along axis A-A as seen in FIG. 13A. In FIG. 13B, the cap 101 holds an abutment 400 or abutment analog 400 (analogous to an abutment) which is adapted to hold a crown such that modifications may be made to the crown. Alternatively, the shape of the abutment 400 may be modified (individualized).

In FIG. 13B, the abutment 400 may also be provided with a screw 401 that is held in a hollow portion of the abutment 400 and protrudes from said abutment 400 such that it may interact with, and be screwed into the threaded portion of the cap 1013, thus holding the abutment 400 securely in the cap 101.

The outer circumference of the blind hole 1011 may also be shaped to match the outer circumference of an implant shoulder. The inserted abutment can therefore be flush with the top surface of the cap 101, which is advantageous when scanning a dental object (crown, abutment or healing abutment). The blind hole 1011 may also be machined such that the internal surface structure corresponds to the internal geometry of an implant.

Figure 14A:
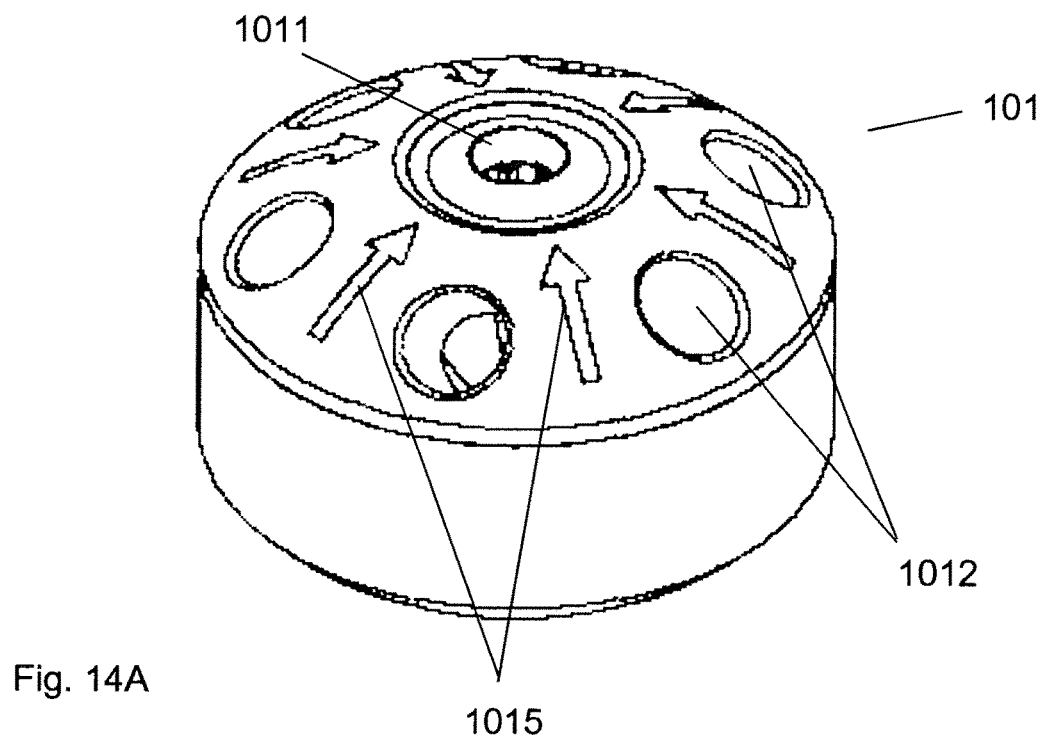
FIGS. 14A and 14B provide an elevated and bird's eye view respectively of an embodiment of the cap wherein additional markings may be seen on said cap.
Figure 14B:
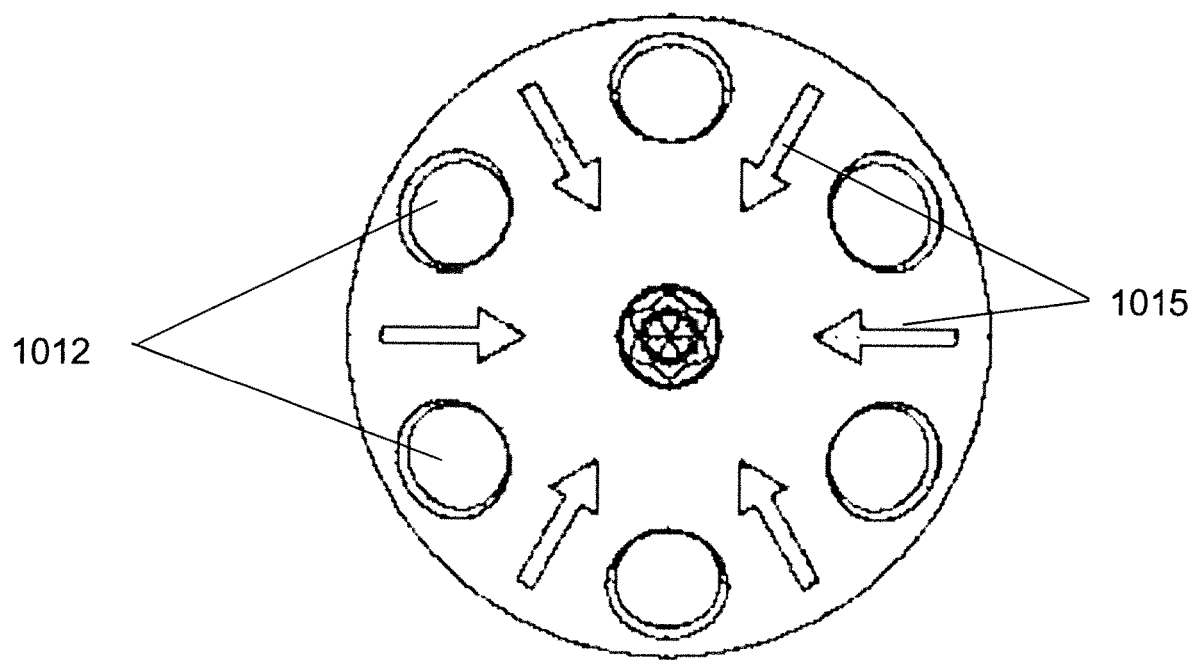

FIGS. 14A and 14B provide an elevated and bird's eye view respectively of an embodiment of the cap 101 wherein additional markings 1015 may be seen etched into the surface of said cap 101. Alternatively, such markings 1015 may also be of different colours or shapes as well as being embossments. Said markings 1015 may provide information to the user such as, for example, arrows directing the user as to where to insert the implant driver 300 or abutment 400 when intended to be held in the blind hole 1011 or cap cavity, such that the channels 1012 used for cleaning and sterilization are not confused with said blind hole 1011.

Alternatively, markings 1015 may provide other information such as an indication of the internal surface structure of the blind hole 1011, in particular the orientation of the anti-rotational features of the implant. It is also possible that one of the markings 1015 is marked or specially designed. This makes it possible to individualize or work on an abutment 400, healing abutment 400 or a crown in the correct position. In addition, a scan of an abutment/crown can be made (e.g. with an intraoral scanner), whereby the exact position is then saved in relation to the geometry of the blind hole 1011, corresponding to the inner geometry of the implant.

FIGS. 15A and B provide views of the shaft 103, 203 of a handle driver 100, 200 embodiment, wherein FIG. 15C provides a cross-sectional view of the mounting portion of the distal end of the shaft 103, 203 along axis A-A as indicated in FIG. 15B.

The interface portion 1031, 2031 may comprise a plurality of grooves that are designed to be gripped by teeth of a ratcheting device (also referred to as ratchet), such that when a ratcheting device is rotated in one direction, the torque is transferred to the handle driver 100, 200, and thus the implant driver 110.

FIG. 15C provides details of the internal structure 205, 206, 207, 208 of the mounting portion and shows at least one of the side openings 206 which extend along the shaft 103, 203. In addition, it displays the distal end of said mounting section which may be referred to as the shaft drive portion 105, 205 and receives the retention element 104, 204 when it is inserted.

FIG. 16A provides a cross-sectional view of an embodiment of the handle driver 100 according to the present invention and FIG. 16B provides a magnification of at least part of the mounting portion (detail X) of the handle driver 100 seen in FIG. 16A.

As can be seen in FIG. 16B, the retention element 104, 204 of FIG. 8 is held in the mounting section. It may also be seen that at least part of the side opening 206 in the mounting section extends further along the shaft 103, 203 than the retention element 104, 204 when fully inserted. This provides a further gap to ensure that fluid may be passed from the outside of the shaft 103, 203 into and around the insides of the shaft 103, 203.

It is noted that herein different embodiments of the handle driver 100,200, cap 101, 201, retention element 104, 204 etc, have been outlined. It should be understood that unless otherwise stated, these embodiments may be used with one another, and the invention is not limited to the combinations seen in the figures.

REFERENCE NUMERALS 100, 200 Handle driver/dental tool
101, 201 Cap
1011 Blind hole
1012 Channels
1013 Cap insert portion
1014 Hole screw thread portion
1015 Markings
2011 Cap screw thread
102/202 Handle
1021, 2021 Internal handle surface
103, 203 Shaft
1031, 2031 Interface portion
104, 204 Retention element
1041 Retention element flexible connecting strips
2041 Retention element proximal end portion
2041a Second opening
2043 Retention element distal end portion
2045 Retention element middle portion
2045a Retention opening
2049 Retention element wider middle portions
105, 205 Shaft drive portion
106, 206 Side opening/Windows 207, 208 Internal surface portions
109, 209 Shaft proximal end
110 implant driver
112, 212 cavity
300 Implant driver for use with ratchet
301 Implant driver head
302 Implant driver distal end
400 Abutment
401 Screw

The invention claimed is:

1. A tool for use in dental implant treatments, the tool comprising:
   a handle;
   a shaft connected to the handle, the shaft comprises a mounting section on the distal end thereof, the mounting section comprising:
      a cavity that is present at the distal end of the shaft and extends from a most distal end surface into, and through, the shaft such that the shaft is hollow for at least a portion of the way through the shaft, and
      at least one side opening is formed in an outer surface of the distal end of the shaft and extends along the shaft; and
   a retention element configured to be held inside the mounting section of the shaft and configured to hold an implant driver;
   wherein:
      the handle, the shaft, and the mounting section are aligned along a longitudinal direction of the tool;
      the retention includes two end portions and a middle portion having an outer diameter narrower than that of the end portions, the middle motion and at least one of the end portions being hollow such that the implant driver may be received within the retention element;
      the middle portion of the retention element is flexible and radially expandable such that insertion of the implant driver into the retention element pushes the narrower middle portion of the retention element outwards, and the implant driver is held inside the retention element via friction;
      the shaft includes a shaft drive portion that is configured to engage and transmit torque to implant driver held by the retention element to drive the implant driver in the dental implant treatments; and
      the shaft drive portion is an internal surface of the shaft distal of the retention element that is configured to engage and transmit torque to an outer surface of the implant driver at a position where the implant driver extends outside of the retention element along a longitudinal axis of the shaft.

2. The tool of claim 1, wherein both of the end portions of the retention element are hollow.

3. The tool of claim 1, wherein the end portions of the retention element are radially compressible and the inner cross section of the mounting section of the shaft is narrower in diameter than the end portions, such that the retention element is held in the mounting section due to friction at both of the end portions.

4. The tool of claim 3, wherein the at least one side opening of the mounting section extends further along the shaft than a proximal end portion of the retention element when the retention element is held in the shaft.

5. The tool of claim 1, wherein the retention element comprises one or more retention openings in an external surface of the middle potion.

6. The tool of claim 5, wherein a number of the one or more retention openings in the retention element differs from a number of the at least one side opening in the mounting section.

7. The tool of claim 6, wherein the retention element comprises four retention openings and the mounting section comprises three side openings.

8. The tool of claim 1, wherein:
   the handle is connected to a cap, and
   the cap comprises a blind hole configured to hold an abutment or other dental instruments.

9. The tool of claim 8, wherein a proximal circumference of the blind hole is configured to receive an implant shoulder.

10. The tool of claim 8, wherein the cap comprises one or more channels that extend from a surface of the cap to a bottom of the blind hole.

11. The tool of claim 8, wherein the cap is fixed to the handle by an adhesive or by laser welding.

12. The tool of claim 8, wherein the cap comprises one or more markings that convey information to a user regarding the blind hole.

13. The tool of claim 1, wherein the tool is shaped as a screwdriver or handle driver.

14. The tool of claim 1, wherein the middle portion of the retention element includes a curved internal surface.

* * * * *